United States Patent [19]

Rollin et al.

[11] Patent Number: 5,612,296
[45] Date of Patent: Mar. 18, 1997

[54] ASHLESS DISPERSANTS THEIR PREPARATION AND THEIR USE

[75] Inventors: Anthony J. Rollin; Joseph J. Valcho, both of Midlothian, Va.

[73] Assignee: Ethyl Corporation, Richmond, Va.

[21] Appl. No.: 566,264

[22] Filed: Dec. 1, 1995

Related U.S. Application Data

[62] Division of Ser. No. 447,308, May 22, 1995, Pat. No. 5,496,480, which is a division of Ser. No. 77,724, Jun. 16, 1993, Pat. No. 5,433,875.

[51] Int. Cl.$^6$ ............. C10M 133/56; C07C 69/34; C07C 69/52
[52] U.S. Cl. ............. 508/240; 508/477; 560/190; 560/198
[58] Field of Search ............. 508/240, 477; 560/190, 198

[56] References Cited

U.S. PATENT DOCUMENTS

| | | | |
|---|---|---|---|
| 3,576,743 | 4/1971 | Widmer et al. | 508/240 |
| 3,632,511 | 1/1972 | Liao | 508/240 |
| 4,814,540 | 3/1989 | Watanabe et al. | 585/523 |
| 5,137,980 | 8/1992 | DeGonia et al. | 508/240 |

*Primary Examiner*—Jerry D. Johnson
*Attorney, Agent, or Firm*—Dennis H. Rainear

[57] ABSTRACT

Ashless dispersants are formed using polymers of propylene characterized in that they are liquid substantially linear polymers, they have stereo-irregularity in the polymer chain, at least 60 mol percent of the polymer has a terminal vinylidene group and, optionally, the polymer contains up to 25 mol percent of ethylene or a $C_4$ to $C_{10}$ monoolefin polymerized into the polymer chains.

6 Claims, No Drawings

ASHLESS DISPERSANTS THEIR PREPARATION AND THEIR USE

This application is a divisional of application Ser. No. 08/447,308 filed May 22, 1995, now U.S. Pat. No. 5,496, 480, which was a divisional of application Ser. No. 08/077, 724 filed Jun. 16, 1993, now U.S. Pat. No. 5,433,875.

TECHNICAL FIELD

This invention relates to ashless dispersants for use in oleaginous media, notably oils of lubricating viscosity, and hydrocarbonaceous fuels such as middle distillate fuels and heavier burner fuels.

BACKGROUND

Chemical additives for lubricating oils are used to control the physical and chemical properties of lubricating oils. These additives are used to modify oil viscosity and viscosity index, to make the oils more resistant to oxidation, and to keep engines and other mechanical equipment clean and protected against corrosion and wear. Water-soluble additives are also commonly used in applications ranging from aqueous hydraulic fluids to household cleaners and cosmetics.

Hydrocarbon-based chemical additives are designed for specific functions by choosing a hydrocarbon type and molecular weight range or molecular weight distribution to allow the additives to function in the fluid type of interest. For instance, high molecular weight polymers can be used to increase viscosity and viscosity index of mineral oils or synthetic oils. Water soluble polymers of polar compounds can be used to thicken water, or even allow water to be pumped more easily. Polar head groups can be designed to be attached to low or high molecular weight hydrocarbon tails to achieve detergency, dispersancy, antiwear or anticorrosion performance.

The hydrocarbon tail can be derived from natural fats or oils, or from petroleum fractions. Synthetic tails can be assembled by the polymerization of olefins or functionalized olefins or by polycondensation of difunctionalized olefins or saturated compounds.

The patent literature frequently describes the use of polymers of olefins having 2 to 6 carbon atoms for use as oil-soluble tails suitable for use in making oil additives. Indeed, some patents refer to use of polymers of even longer chain olefin monomers for this purpose. Extensive use is made of ethylene and butene or isobutylene oligomers in forming oil additives. High molecular ethylene-propylene olefin copolymers are commonly used to increase the viscosity index of lubricating oils. Propylene trimer and tetramer have been used as low molecular weight tails, and technology to make branched $C_{20}$ to $C_{100}$ polypropylene has been developed.

Despite the vast amount of work conducted heretofore, a need exists for novel ashless dispersants that have enhanced thermal stability and/or that can enable use of smaller amounts of viscosity index improvers in formulating finished lubricants, giving a cost reduction. Because of the relatively high temperatures to which finished lubricating oils are exposed during actual service conditions, improved thermal stability is a desirable property in ashless dispersants. The advantages of having an ashless dispersant which contributes viscosity increase to the lubricant and thus reduces the amount of viscosity index improver needed in the finished oil is referred to, for example, in U.S. Pat. No. 4,234,435.

THE INVENTION

This invention is deemed to fulfill the foregoing need by providing and utilizing an ashless dispersant having in its chemical structure at least one aliphatic substituent derived from a special type of polymer. The special polymers used in forming the dispersants are polymers of propylene characterized in that (a) they are liquid substantially linear polymers, (b) they have stereo-irregularity in the polymer chain, (c) at least sixty mol percent, preferably at least 75 mol percent and more preferably at least 85 mol percent of the polymer has a terminal divalent methylene group ($=CH_2$), and (d) optionally, they contain up to 25 tool percent of ethylene or a $C_4$ to $C_{10}$ monoolefin polymerized into the polymer chains. Preferred ashless dispersants are formed from polypropyl lens homopolymer satisfying the foregoing requirements (a) (b) and (c).

As to type, the ashless dispersants of this invention can be succinic eater-amide dispersants, succinimide dispersants, Mannich base dispersants, succinic amide-triazole dispersants, or succinic triazole dispersants. Process technology that can be adapted for producing these various types of dispersants can be found in the literature. For example, an ene reaction (sometimes referred to as a thermal reaction) between the special polymer of propylene and maleic anhydride yields an alkenyl-substituted succinic anhydride. This then can be converted into an alkenyl succinic ester-amide using conditions such as are described in U.S. Pat. Nos. 3,219,666; 3,282,959; 3,640,904; 4,426,305 or 4,873,009; or into an alkenyl succinimide using conditions such as are described in U.S. Pat. Nos. 3,172,892; 3,219,666; 3,272, 746; to 4,234,435; or into an alkenyl succinic triazole or alkenyl succinic amide-triazole dispersant (depending upon reaction proportions employed) using conditions such as are described in U.S. Pat. Nos. 4,908,145 or 5,080,815. By alkylating a phenolic compound with a special propylene polymer as described above using a Lewis acid catalyst such as $BF_3$ or $AlCl_3$, and using reaction conditions such as are described in U.S. Pat. No. 3,736,353, an alkyl-substituted phenol is formed. Then by employing known reaction conditions such as are described in U.S. Pat. No. 3,736,357, the alkylated phenol is reacted with an aldehyde such as acetaldehyde, propionaldehyde, butyraldehyde, valeraldehyde, furfuryl aldehyde, etc., but preferably formaldehyde or a formaldehyde-producing reagent such as para-formaldehyde, formalin, etc., and a polyamine or a polyhydroxy-substituted amine, a Mannich base dispersant of this invention is formed.

The ashless dispersants of this invention can be post-treated (i.e., reacted) with various post-treating agents such as are referred to in U.S. Pat. Nos. 4,234,435 or 5,137,980. Preferred post-treated ashless dispersants of this invention are those which have been borated by reaction with a suitable boron-containing material, such as boric acid or other boron acids, boron oxide, boron trihalides, ammonium borate, super-borated ashless dispersants, etc. Generally speaking, the borated ashless dispersants will contain from about 0.01 to about 1% by weight of boron and preferably from about 0.05 to about 0.5 weight % of boron based on the weight of the active dispersant (i.e., omitting from consideration the weight of any diluent or unreacted components that may be present in the dispersant).

In general, the ashless dispersants producible pursuant to this invention are characterized by having enhanced thermal stability, by having relatively high useful viscosities when employed in lubricating oil, and by possessing good dispersancy effectiveness. In addition, ashless dispersants of this invention can be produced having good shear stability. Moreover, it is possible to produce ashless dispersants of this invention having better handleability (e.g., lower viscosities at low temperatures) than comparable dispersants made from polyisobutylene.

Accordingly, as compared to the same ashless dispersant made with a polypropylene of the same number average molecular weight 3.5 but not meeting the combined requirements of (a), (b), and (c) above, the dispersants of this invention tend to have higher thermal stabilities, higher useful viscosities, at least equivalent dispersancy, and equal or better shear stability. And as compared to the same ashless dispersant but made with a polyisobutene of the same number average molecular weight, the dispersants of this invention tend to have lower viscosities at low temperatures, and thus better handleability at low temperatures.

In contrast to stereo-regular polypropylene such as obtained with Ziegler-Natta catalysts, the polymers of propylene used pursuant to this invention are formed by a route that gives a substantially linear product having a controlled amount of branching. The homopolymers of this type are preferred over the copolymers of this type as the former tend to form ashless dispersants that have the highest useful viscosities and thus these dispersants offer the advantage of enabling use of smaller amounts of VI improvers. Typically these homopolymers contain an average in the range of about 15 to about 250 propylene moieties in the polymer chains. U.S. Pat. No. 4,814,540 describes one method which may be used to form such polymers.

Polyamines (including polyether polyamines) and polyhydroxy amines that can be used in forming the dispersants of this invention have at least one primary or secondary amino group in the molecule. Amines of this type and also polyols that can be used forming ester-amide dispersants of this invention are extensively described in the patent literature, such as, for example U.S. Pat. Nos. 4,234,435, 4,873,009 and 5,137,980.

Accordingly, among the embodiments of this invention is an ashless dispersant having in its chemical structure at least ones aliphatic hydrocarbyl substituent derived from a liquid, substantially linear polymer of propylene, said polymer having stereo-irregularity and optionally containing up to 25 mol percent ethylene or $C_4$ to $C_{10}$ monoolefin polymerized into the polymer chain, at least 60 mol percent of said polymer having a terminal vinylidene group, said dispersant being a Mannich base formed from (i) a phenol having said aliphatic substituent thereon, (ii) an aldehyde, and (iii) an amine selected from polyamines and polyhydroxy amines. In these dispersants the preferred aldehyde is formaldehyde or a formaldehyde-forming reagent and the preferred amine is a polyamine, most preferably an ethylene polyamine such as diethylenel triamine, triethylene tetramine, tetraethylene pentamine, or pentaethylene hexamine.

Another embodiment is an ashless dispersant having in its chemical structure at least one aliphatic hydrocarbyl substituent derived from a liquid, substantially linear polymer of propylene, said polymer having stereo-irregularity and optionally containing up to 25 mol percent of ethylene or $C_4$ to $C_{10}$ monoolefin polymerized into the polymer chain, at least 60 mol percent of said polymer having a terminal vinylidene group, said dispersant being a succinic ester-amide formed from (i) an alkenyl succinic acylating agent having said substituent thereon and (ii) an N-substituted poly(hydroxyalkyl) amine or a combination of a polyamine and a polyol, which polyamine and polyol are reacted with said acylating agent concurrently or sequentially in any order. Of these dispersants, it is preferable to react the acylating agent with an alkylene diamine having 4 to 12 carbon atoms in the molecule and at least about 2.5 hydroxyalkyl groups per molecule in accordance with the teachings of U.S. Pat. No. 4,873,009. Most preferred dispersants of this type are formed by reacting the acylating agent with hexamethylene diamine having about 3 hydroxyalkyl groups per molecule.

Still another embodiment of this invention is an ashless dispersant having in its chemical structure at least one aliphatic hydrocarbyl substituent derived from a liquid, substantially linear polymer of propylene, said polymer having stereo-irregularity and optionally containing up to 25 mol percent of ethylene or $C_4$ to $C10$ monoolefin polymerized into the polymer chain, at least 60 mol percent of said polymer having a terminal vinylidene group, said dispersant being a succinimide formed from (i) an alkenyl succinic acylating agent having said substituent thereon and (ii) a polyamine having at least one primary amino group in the molecule. Preferably the polyamine used is at least one cyclic or acyclic ethylene polyamine having an average of from 3 to 6 nitrogen atoms per molecule. It is even more preferably to employ ethylene polyamines selected from diethylene triamine, triethylene tetramine, tetraethylene pentamine, and pentaethylene hexamine.

A further embodiment of this invention is an ashless dispersant having in its chemical structure at least one aliphatic hydrocarbyl substituent derived from a liquid, substantially linear polymer of propylene, said polymer having stereo-irregularity and optionally containing up to 25 mol percent of ethylene or $C_4$ to $C_{10}$ monoolefin polymerized into the polymer chain, at least 60 mol percent of said polymer having a terminal vinylidene group, said dispersant being a product formed by reacting (i) an alkenyl succinic acylating agent having said substituent thereon and (ii) a basic salt of aminoguanidine wherein the molar ratio of said aminoguanidine to said acylating agent is in the range of about 1.4:1 to about 2.2:1 such that the product obtained upon reaction thereof exhibits a dominant infrared peak at 1640 $cm^{-1}$. Preferably, the basic salt of aminoguanidine used is aminoguanidine bicarbonate.

A still further embodiment of this invention is an ashless dispersant having in its chemical structure at least one aliphatic hydrocarbyl substituent derived from a liquid, substantially linear polymer of propylene, said polymer having stereo-irregularity and optionally containing up to 25 tool percent of ethylene or $C_4$ to $C_{10}$ monoolefin polymerized into the polymer chain, at least 60 tool percent of said polymer having a terminal vinylidene group, said dispersant being a product formed by reacting (i) an alkenyl succinic acylating agent having said substituent thereon and (ii) a basic salt of aminoguanidine wherein the molar ratio of said aminoguanidine to said acylating agent is in the range of about 0.4:1 to about 1.3:1. Preferably, these products exhibit an infrared spectrum having peaks in the region of about 1580 and about $1690^{-1}$. Another preferred product of this type yields an infrared spectrum having a peak in the region of about 1720 cm⁻.

Yet another embodiment of this invention is an ashless dispersant having in its chemical structure at least one aliphatic hydrocarbyl substituent derived from a liquid, substantially linear polymer of propylene, said polymer having stereo-irregularity and optionally containing up to 25 tool percent of ethylene or $C_4$ to $C_{10}$ monoolefin polymerized into the polymer chain, at least 60 mol percent of said polymer having a terminal vinylidene group, said dispersant being further characterized by having a higher thermal stability than an identical ashless dispersant formed from stereo-regular polymer of propylene in which at least 60 tool percent of the polymer has an internal olefinic double bond.

Preferably, the substantially linear polymer of propylene used in making all of the foregoing dispersants is a homopolymer.

Another embodiment of this invention comprises the use of from 0.5 to 20% by weight, and preferably from 3 to 15% by weight, of an ashless dispersant of this invention in an oil of lubricating viscosity in order to provide a viscosity increase to said oil, and thereby to enable a reduction in the amount of viscosity index improver required to achieve a target viscosity.

The use of from 0.5 to 20% by weight, and preferably from 3 to 15% by weight, of an ashless dispersant of this invention in an oil of lubricating viscosity subjected to an elevated temperature (e.g., at least 200° C. and preferably at least 250° C.) during use to provide dispersancy without substantial thermal degradation of the dispersant, is another embodiment of this invention.

A still further embodiment of this invention is the use in forming an ashless dispersant of a liquid, substantially linear polymer of propylene to create a substituent of said ashless dispersant that renders the dispersant capable of providing a beneficial viscosity increase in an oil of lubricating viscosity when the dispersant is dissolved therein at a concentration within the range of 0.5 to 20% by weight, said polymer having stereo-irregularity and optionally containing up to 25 mol percent of ethylene or $C_4$ to $C_{10}$ monoolefin polymerized into the polymer chain, at least 60 mol percent of said polymer having a terminal vinylidene group.

Preferred dispersants of this invention are those that have the ability to increase the 100° C. kinematic viscosity of an additive-free the range of 5.0 to 5.5 cSt by at least 50%, more preferably by at least 60%, and most preferably by at least 70%, when dissolved therein at a concentration of 3.5 wt % based on the total weight of the resulting solution.

These and other embodiments will be apparent from a consideration of this specification and the appended claims.

The following examples illustrate the practice and advantages achievable by the practice of this invention. These examples are not intended to limit, do not limit, and should not be construed as limiting the generic scope of this invention.

EXAMPLE 1

A mixture of 24.6 g (0.02 mol) of a liquid polypropylene and 5.8 g (0.06 mol) of phenol together with 3.1% of boron trifluoride i complexed with phenol was stirred for 2.5 hours at 49° C. This polypropylene, prepared by Amoco Chemical Company, was substantially linear and had stereo-irregularity in the polymer chains. Its number average molecular weight by gel permeation chromatography was 1230, and 95% of the polymer was unsaturated with more than 90% of the chains terminated with a divalent methylene group (=$CH_2$) as part of a vinylidene structure (>C=$CH_2$). At the end of the 2.5 hour period, the catalyst was neutralized with gaseous ammonia, and the excess; phenol was stripped with nitrogen to 177° C. yielding 26 g of alkylated phenol product. The product was then filtered yielding 22 g of filtered alkylated phenol product.

EXAMPLE 2

To a mixture of 17.7 g (0.01 mol) of the product of Example 1, 4 xylene, 1.16 g (0.01 mol) of diethylene triamine, and 0.31 g (0.001 mol) of oleic acid, at 88° C. was added 3.02 g (0.037 mol) of 37% formalin. After 1 hour at 92° C., the mixture was warmed 166° C. and stirred for 3 hours to give 17.7 g of Mannich base dispersant of this invention.

EXAMPLE 3

A mixture of 40 g (0.013 mol) of a liquid polypropylene and 3.9 g (0.04 mol) of phenol/borontrifluoride complex was reacted for 3 hours at 49° C. This polypropylene, also supplied by Amoco Chemical Company, had the same characteristics as that used in Example 1 above, except that the polymer was more viscous (1047 cSt at 100° C.; 117,715 cSt at 40° C.), had a molecular weight as determined by vapor phase osmometry of 2225 and was 91% unsaturated. It had a viscosity index of 126. At the end of the 3-hour reaction period, the product was neutralized with gaseous ammonia, and the product was stripped to 177° C. to give 40.5 g of alkylated phenol product.

EXAMPLE 4

At 88° C., 1.24 g (0.015 reel) of formalin was added to a mixture of 32 g (0.008 mol) of the alkylated phenol of Example 3, 1.44 g (0.008 tool) of tetraethylene pentamine, 0.85 g (0.003 tool) of oleic acid, and 14 g of 95 Neutral Mid-continent base oil. After 1 hour at 116° C., the mixture was warmed to 155° C., and 1.86 g (0.023 mol) of formalin was added. After 2 hours at 155° C., the product (47.5 g) was filtered. The Mannich base dispersant of this invention so formed had a TBN of 16 by ASTM D2896.

EXAMPLE 5

The procedure of Example 3 was repeated except that the alkylation was conducted in 40 mL of heptane.

EXAMPLE 6

The procedure of Example 4 was repeated but with the addition to the reaction system of 25 mL of heptane as a diluent, and using 30.6 g (0.009 mol) of the product of Example 5 that had been stripped to 177° C. with nitrogen. The Mannich base product of this invention formed in this manner was produced in a yield of 45.5 g, and it had a TBN of 22.

COMPARATIVE EXAMPLE A

A mixture of 24.6 g (0.02 mol) of Ultravis 30 polybutene supplied by BASF and 5.8 g (0.06 mol) of phenol/borontrifluoride complex was stirred for 2.5 hours at 49° C. This polybutene had a number average molecular weight of 1230, contained more than 95% unsaturation, and had more than 70% vinylidene end groups. After neutralization with ammonia, the product was stripped to 177° C. to yield 25.6 g of a long-chain alkylphenol formed from polybutene.

COMPARATIVE EXAMPLE B

At 88° C., 1.36 g (0.034 mol) of formalin was added to a solution of 14.6 g (0.01 mol) of the product of Comparative Example A, 1.05 g (0.01 mol) of diethylene triamine, 0.29 g (0.001 mol) of oleic acid, and 4 mL of xylene. After 1 hour at 92° C., the mixture was stripped to 166° C. and stirred for 3 hours to yield a Mannich base dispersant having a long-chain derived from polybutene.

COMPARATIVE EXAMPLE C

Polybutene having a number average molecular weight of 2100, sold by Amoco Chemical Company as H-1500 polybutene, was reacted with phenol in the presence of borontrifluoride complex to give an alkylated phenol using reacting conditions described in U.S. Pat. No. 3,736,357.

COMPARATIVE EXAMPLE D

A Mannich base dispersant was prepared by the reaction of thee alkylated phenol of Comparative Example C with tetraethylene pentamine and formaldehyde as described in U.S. Pat. No. 3,736,357. The product was then borated to yield a boronated Mannich base dispersant having a long-chain derived from polyisobutylene.

COMPARATIVE EXAMPLE E

The procedure of Comparative Example D was repeated except that E-100 polyethylene polyamine bottoms from Dow Chemical Company was used as the amine source, and the Mannich base dispersant was not subjected to boration.

The products produced as in Examples 4, 6, and Comparative Example D were blended at 8% by weight into a Mid-Continent bases oil having a 100° C. viscosity of 5.45 cSt. The blend with the ashless dispersant of Example 4 had a viscosity of 9.26 cSt at 100° C., and the blend with the ashless dispersant of Example 6 gave a viscosity of 8.95 cSt at 100° C., while the dispersant of Comparative Example D gave a viscosity of 7.25 cSt at 100° C. These respective dispersants were of nearly equal activities and were derived from polymers of nearly equal molecular weights. That is, the dispersants of Examples 4 and 6 had a content of active dispersant of 42 weight % whereas the dispersant of Comparative Example D had a content of active dispersant of 40 weight %. And it will be noted that the Mannich dispersants of this invention (Examples 4 and 6) gave higher 100° C. viscosities than the dispersant of Comparative Example D by virtue of the advantageous special structure of the polypropylene used in forming the dispersants of Examples 4 and 6.

The products made as in Examples 4, 6 and Comparative Example D were then blended into a 5W-30 motor oil formulated with metal-containing phenates and sulfonates, zinc dithiophosphate wear inhibitors, sulfur-containing antioxidant and a viscosity index improver supplied by Shell Chemical Company (Shellvis 200C). With of the dispersant of Comparative Example D, 6.5% of the viscosity index improver was necessary to meet a viscosity target of 11.2 cSt at 100° C. On the other hand, with the product of Example 6 at 8% concentration in the finished oil, and only 5.5% by weight of the same viscosity index improver, the oil viscosity was well above the 11.2 cSt target—this oil had a viscosity of 13.4 cSt at 100° C. These results thus show the ability of the dispersants of this invention to contribute significant viscosity index credit to the oil and thereby enable reduction of the amount of the conventional viscosity index improver needed to achieve the desired viscosity target. Reducing the amount of viscosity index improver in a motor oil can thus offer both cost and engine cleanliness advantages.

The ability of the dispersants of this invention to disperse engine sludge was measured in a bench test where 5 to 6% of a test dispersant is added to a severe used oil from a Sequence VE engine test. This used oil is viscous and serves as a source of engine sludge. The dispersant and used VE oil are heated, shaken, and stored overnight at 149° C. After again shaking, seven drops of the oil are dropped onto Whatman No. 3031 915 blotter paper. After 16 hours, the diameters of the inner ring of dispersed sludge and outer oil ring are measured. The percent spot dispersancy is the diameter of the inner ring, divided by the diameter of the outer ring, times 100. Without dispersant, values of 36 to 38% are obtained. Values above 70% with 5 or 6% added dispersant are indicative of good dispersancy. This test procedure is described in Example 1 of U.S. Pat. No. 4,908,145.

The product of Comparative Example D added at 6. and 5% gave percent spot dispersancies of 83 and 79%, respectively. This product exhibits excellent properties in the Sequence VE test and the Sequence IIIE test. It also exhibits excellent diesel engine performance. The products formed as in Example 6 at 6 and 5 % gave percent spot dispersancies of 86 and 81% showing that excellent dispersancy is likewise achieved by this dispersant of this invention. The product of Example 4 exhibited percent spot dispersancies of 76 and 63 at 6 and 5 % respectively. Thus it also exhibited good dispersancy, albeit somewhat less than that of the product of Example 6.

The excellent thermal stability achievable by the practice of this invention was shown by the use of a hot tube test using an oil formulated for use in locomotive engines as described in U.S. Pat. No. 4,948,523. In this test, the formulated oil is pumped through a small-bore glass tube heated at 296° C. over a 16-hour period. Them deposits are visually rated on a scale of 0 to 10, with 10 being clean. The dispersant of this invention produced as in Example 6 gave ratings of 7.5 and 8.0 in repeat tests. In contrast, the ashless dispersant produced as in Comparative Example E gave ratings of 4.0 and 0.5.

In addition to the foregoing advantages achievable by the practice of this invention is the fact that propylene has been historically less expensive that isobutylene or even a mixed stream) of butenes. This cost differential may increase in the future as the use of isobutylene and other butenes is increased to make oxygenated blending agents, such as methyl tert-butyl ether for use in gasoline and other fuels.

In formulating finished lubricating oils containing one or) more of the ashless dispersants of this invention, various other additive components can be utilized. These include low-base and) the sulfonates, sulfurized phenates and salicylates of lithium, sodium, potassium, calcium and/or magnesium, and the alkaline earth metal calibrates (note U.S. Pat. Nos. 5,114,601 and 5,205,946); antiwear and/or extreme pressure agents such as metal salts of dihydrocarbyl dithiophosphoric acids (e.g., zinc, copper or molybdenum dialkyldithiophosphates); oxidation inhibitors such as hindered phenolic antioxidants, aromatic amine antioxidants, sulfur-containing antioxidants, and copper-containing antioxidants; supplementary dispersants such as succinimide dispersants, succinic ester-amide dispersants, and Mannich base dispersants; friction reducing and/or fuel economy improving additives such as glycerol) monooleate, pentaerythritol monooleate, long chain acid esters of) glycols, sulfurized olefins, sulfurized unsaturated fatty acids and sulfurized unsaturated fatty acid esters; rust and corrosion inhibitors; foam inhibitors; viscosity index improvers; polymeric dispersant-viscosity index improvers; demulsifying agents; and the like. Such additives can be employed in the base oil at their customary use concentrations, which are known to those skilled in the art and reported in numerous patent disclosures. For further details concerning such additives, one may refer for example to U.S. Pat. Nos. 4,664,822; 4,908,145; 5,080,815 and 5,137,980.

The base oils used in formulating finished lubricants containing the ashless dispersants of this invention can be derived from petroleum (or tar sands, coal, shale, etc.). Likewise, the base oils can be or include natural oils of suitable viscosities such as rapeseed oil, etc., and synthetic oils such as hydrogenated poly-olefin oils; poly-$\alpha$-olefins (e.g., hydrogenated or unhydrogenated $\alpha$-olefin oligomers such as hydrogenated poly-1-decene); alkyl esters of dicarboxylic acids; complex esters of dicarboxylic acid, polyglycol and alcohol; alkyl esters of carbonic or phosphoric acids; polysilicones; fluorohydrocarbon oils; and the like. Mixtures of mineral, natural and/or synthetic oils in any suitable proportions are also useable. The term "base oil" for this disclosure includes all the foregoing. In most cases the base oil is preferably a petroleum-derived mineral oil of the types conventionally used in forming passenger car or heavy duty diesel engine oils. The fact that the base oils used in the compositions of this invention may be composed of (i) one or more mineral oils, (ii) one or more synthetic oils, (iii) one or more natural oils, or (iv) a blend of (i) and (ii), or (i) and (iii), or (ii) and (iii), or (i), (ii) and (iii) does not mean that these various types of oils are necessarily equivalents of each other. Certain types of base oils may be used for the specific properties they possess such as biode-gradability, high temperature stability, or non-flammability. In other compositions, other types of base oils may be preferred for reasons of availability or low cost. Thus, the skilled artisan will recognize that while the various types of base oils discussed above may be used in the compositions of this invention, they are not necessarily equivalents of each other in every instance.

The ashless dispersants of this invention can be blended into oils of lubricating viscosity separately and apart from other additive components. Preferably however, the dispersants are formulated into an additive concentrate or "package" which is them used in formulating the finished lubrication compositions. The package will usually contain up to 50 wt % of diluent with the balance being the active additive components, namely, at least one dispersant of this invention and optionally, but preferably, one or more other additive components, such as those referred to above and/or in various patents cited herein. From 5 to 60 wt % of the concentrate can be one ore more dispersants of this invention. This invention also provides a composition which consists of 1 to 99 wt % of an active dispersant of this invention and from 99 to 1 wt % of diluent oil. Other additives, including diluents that may be associated therewith, can be blended into such compositions to form additive packages of this invention.

The dispersants of this invention can also be used as additives in hydrocarbonaceous fuels such as gasoline, diesel fuel, gas oils, jet fuels, cycle oils, burner fuels, bunker fuels, and the like. Amounts within the range of 0.5 to 10% by weight will usually be employed, although departures from this range can be made.

Lower molecular weight versions of the polymers of propylene referred to hereinabove can be used an alkylation of aromatic hydrocarbons. These alkylated materials (e.g., alkylated benzene, alkylated toluene, alkylated xylenes, etc.) can then be sulfonated and overbased to form highly useful alkali or alkaline earth metal-containing detergents and rust inhibitors. Alternatively, the polymers of propylene can be used to alkylate hydroxy-substituted aromatic hydrocarbons, which can be sulfurized and neutralized or overbased to form metal-containing phenate detergents.

Except as referred to in the examples, all percentages of the dispersants of this invention are in terms of the weight of active, dispersant in relation to the total weight of the overall composition under discussion.

The complete disclosure of each U.S. Patent cited anywhere hereinabove is incorporated herein by reference as if fully set forth in this specification.

This invention is susceptible to considerable variation in its practice. Accordingly, this invention is not intended to be limited by this specific exemplifications set forth hereinabove. Rather, this invention is intended to embrace the subject matter within the spirit and scope of the appended claims and the permissible equivalents thereof.

What is claimed:

1. An ashless dispersant having in its chemical structure at least one aliphatic hydrocarbyl substituent derived from a liquid, substantially linear polymer of propylene having a controlled amount of branching, said polymer having stereo-irregularity and optionally containing up to 25 mol percent of ethylene or $C_4$ to $C_{10}$ monoolefin polymerized into the polymer chain, at least 60 mol percent of said polymer having a terminal vinylidene group, said dispersant being a succinic ester-amide, formed from (i) an alkenyl succinic acylating agent having said substituent thereon and (ii) an N-substituted poly(hydroxyalkyl) amine or a combination of a polyamine and a polyol, which polyamine and polyol are reacted with said acylating agent concurrently or sequentially in any order.

2. An ashless dispersant according to claim 1 wherein said ashless dispersant is formed by reacting said acylating agent with an alkylene diamine having 4 to 12 carbon atoms in the molecule and at least about 2.5 hydroxyalkyl groups per molecule.

3. An ashless dispersant according to claim 2 wherein said alkylene diamine is hexamethylene diamine having about 3 hydroxyalkyl groups per molecule.

4. An ashless dispersant according to claim 2 wherein said substantially linear polymer of propylene is a propylene homopolymer.

5. A lubricating oil composition containing from 0.5 to 60% by weight of an ashless dispersant of claim 1.

6. A lubricating oil composition containing from 0.5 to 60% by weight of an ashless dispersant of claim 4.

* * * * *